United States Patent [19]
Raulerson et al.

[11] Patent Number: 5,944,732
[45] Date of Patent: Aug. 31, 1999

[54] SUBCUTANEOUS TUNNELLING DEVICE AND METHODS OF FORMING A SUBCUTANEOUS TUNNEL

[75] Inventors: J. Daniel Raulerson, Brewton, Ala.; Anthony J. Madison, Fort Washington; Timothy M. Schweikert, Levittown, both of Pa.

[73] Assignee: Medical Components, Inc., Harleysville, Pa.

[21] Appl. No.: 08/927,392

[22] Filed: Aug. 27, 1997

[51] Int. Cl.⁶ ................................................... A61B 17/32
[52] U.S. Cl. ........................ 606/167; 606/165; 606/168; 604/264; 604/273; 604/274
[58] Field of Search .................... 606/167, 165, 606/168, 190, 191; 604/22, 272, 273, 274, 264

[56] References Cited

U.S. PATENT DOCUMENTS

| | | |
|---|---|---|
| 2,024,982 | 12/1935 | Scott . |
| 3,196,876 | 7/1965 | Miller ........................................ 128/343 |
| 3,336,927 | 8/1967 | Klebanoff . |
| 4,299,228 | 11/1981 | Peters ........................................ 128/348 |
| 4,490,136 | 12/1984 | Ekbladh et al. ........................... 604/22 |
| 4,574,806 | 3/1986 | McCarthy . |
| 4,705,041 | 11/1987 | Kim ........................................... 128/343 |
| 4,972,328 | 11/1990 | Beck et al. . |
| 5,057,075 | 10/1991 | Moncrief et al. . |
| 5,234,438 | 8/1993 | Semrad . |
| 5,306,240 | 4/1994 | Berry . |
| 5,431,661 | 7/1995 | Koch . |
| 5,603,704 | 2/1997 | Brin et al. ................................. 604/281 |

*Primary Examiner*—Michael Buiz
*Assistant Examiner*—Lien Ngo
*Attorney, Agent, or Firm*—Panitch Schwarze Jacobs & Nadel, P.C.

[57] ABSTRACT

A subcutaneous tunnelling device, a dilator and a method of forming a subcutaneous tunnel are provided. The device includes a trocar having a front end with a point configured for piercing skin, and a dilator which has a front end removably attached to the rear end of the trocar. The dilator is for dilating a section of a subcutaneous tunnel and includes a dilating section having a maximum diameter sized for dilating an interior surface of a subcutaneous tunnel for seating a catheter stabilizing cuff in the subcutaneous tunnel. The method of forming a subcutaneous tunnel includes the steps of inserting a trocar through a first location on a cutaneous surface and moving the trocar through subcutaneous tissue to form a subcutaneous tunnel. The trocar is at least partially removed and a front end of a dilator is attached to the trocar. A section of the tunnel is dilated by moving the dilator partially through the tunnel until the front end of the dilator reaches a first subcutaneous location in the tunnel. The dilator and trocar are at least partially withdrawn from the dilated tunnel section of the subcutaneous tunnel through the first end of the tunnel.

23 Claims, 8 Drawing Sheets

SUBCUTANEOUS TUNNELLING DEVICE AND METHODS OF FORMING A SUBCUTANEOUS TUNNEL

BACKGROUND OF THE INVENTION

The present invention relates to a subcutaneous tunnelling device and methods for subcutaneous tunnelling useful for securing and sealing a catheter within the subcutaneous tissue of a patient.

In the medical field, there is often the need to form a subcutaneous tunnel within a patient. Ordinarily, such tunnels are used to secure a catheter or other tubular means inside the body of the patient. Catheters, shunts, drainage tubes and the like, generally referred to herein as catheters, may be located within various sections of the human body for the introduction and removal of fluid from the body.

It is known to use a trocar to create a subcutaneous tunnel and to subsequently use the trocar to pull a catheter through the formed tunnel. When using prior art trocars, which have a circular cross section, a subcutaneous tunnel is created which has a constant inner diameter approximately equal to the maximum outer diameter of the trocar. This inner diameter is intended to approximate the outside diameter of the catheter or other tubular member to be secured in the tunnel.

One common application of subcutaneous tunnels is for securing the proximal end of a catheter when the distal end of the catheter has been inserted into an area of the body, such as a vein. By securing the proximal end of the catheter in some manner, it protects the patient from having the catheter accidentally pulled from the vein. The tunnel is formed and the catheter is positioned in the tunnel, typically by attaching the catheter to one end of a trocar and pulling the catheter through the tunnel. Trocars typically include a piercing point at one end which is used to form the tunnel. The opposite end of the trocar has a single set of threads which are used to grip the interior surface of the catheter to enable the trocar to pull the catheter through the tunnel. To secure the proximal portion of the catheter in the subcutaneous tunnel, many catheters are provided with a fabric tissue ingrowth stabilizing cuff wrapped around a portion of the outside of the catheter which is to be located within the subcutaneous tunnel. The cuff is generally sized to fit snugly in the tunnel or other area. Once in place, the surrounding subcutaneous tissue grows into the cuff thereby sealing the tunnel and securing the proximal portion of the catheter so that it cannot be pulled out during use.

While such subcutaneous tunnelling procedures are effective, they still present some disadvantages. When tunnelling soft durometer catheters, for example, a single catheter of a Tesio catheter assembly, frictional forces created when pulling the large diameter stabilizing cuff through the narrow tunnel with the trocar are difficult to overcome. However, a snug fit is desired in order to seal the tunnel effectively. Occasionally, the proximal portion of such a catheter may snap at the location of the stabilizing cuff where the forces tend to be localized. In such an instance, the physician may have to re-catheterize the patient and remove the broken catheter.

Therefore, there is a need in the art for a method of tunnelling and a tunnelling device which achieves the advantages of the prior art procedures in achieving a snug fit and stabilizing the catheter, but which eliminates disadvantages encountered in tunnelling and placing catheters having such cuffs by reducing the effects of the frictional forces encountered during tunnelling when pulling the catheter and cuff through the tunnel.

BRIEF SUMMARY OF THE INVENTION

The present invention includes a subcutaneous tunnelling device which comprises a trocar and a dilator. The trocar has a front end and a rear end. The front end has a point configured for piercing skin. The dilator has a front end, a rear end and a dilating section disposed between the front end and the rear end. The dilating section has a tapering outside diameter greater than an outside diameter of the trocar. The front end of the dilator is removably attached to the rear end of the trocar.

The invention further includes a dilator for dilating a section of the subcutaneous tunnel. The dilator comprises a front end, which is configured for being removably attached to a trocar, a rear end, and a rigid dilating section disposed between the front end and the rear end.

Also included in the present invention is a method of forming a subcutaneous tunnel. The method comprises inserting a trocar through a first location on a cutaneous surface and moving the trocar through subcutaneous tissue to form a subcutaneous tunnel having a first end near the first location. A dilator having a front end is attached to the trocar. A section of the tunnel is dilated by moving the dilator partially through the tunnel until the front end of the dilator reaches a first subcutaneous location in the tunnel. The dilator and the trocar are at least partially withdrawn from the dilated tunnel section of the subcutaneous tunnel through the first end of the tunnel.

In an alternative method of forming a subcutaneous tunnel according to the present invention, the method comprises the steps of inserting a tunnelling device, including a trocar having a rear end and a dilator having a front end removably attached to the rear end of the trocar, through a first location on a cutaneous surface. The tunnelling device is moved through subcutaneous tissue to form a subcutaneous tunnel having a first end near the first location. A section of the tunnel is dilated by moving the tunnelling device through the tunnel until the front end of the dilator reaches a first subcutaneous location in the tunnel. The tunnelling device is at least partially withdrawn from the dilated tunnel through the first end of the tunnel.

One embodiment of the present invention includes a device for forming subcutaneous tunnel, including a dilated tunnel section, for securing a proximal end of a catheter when a distal end of the catheter is positioned in an area to be catherized. The device comprises a trocar and a dilator. The trocar is for forming a subcutaneous tunnel and has a front end and a rear end. The front end has a point configured for piercing skin. The dilator has a front end, a rear end and a dilating section disposed at the rear end of the dilator. The dilating section has a tapering outside diameter including a maximum diameter sized for dilating an interior surface of the subcutaneous tunnel for seating a catheter stabilizing cuff in the dilated tunnel section. The dilating section of the dilator has a generally octagonal longitudinal cross-section. The front end of the dilator is removably attached to the rear end of the trocar.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings, embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF THE INVENTION

Certain terminology is used in the following description for convenience only and is not limiting. The words "front", "rear", "lower" and "upper" designate directions in the drawings to which reference is made. The words "front", "frontward", "rear" and "rearward" refer to directions toward and away from, respectively, the piercing point of the tunnelling device of the present invention. The words "proximal" and "distal" refer to directions toward and away from, respectively, the insertion end of a catheter located in an area to be catheterized such as a blood vessel. The terminology includes the words above specifically mentioned, derivatives thereof and words of similar import.

Figure 1:
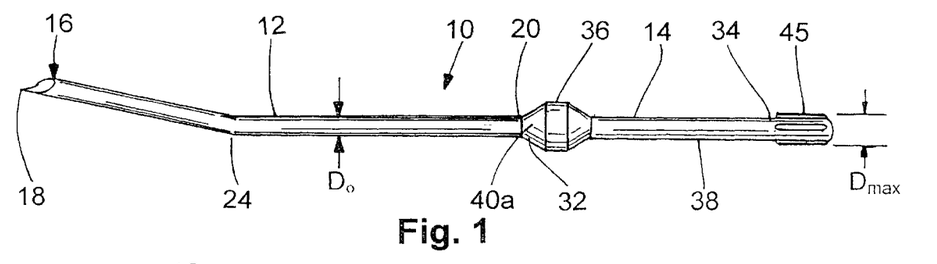
FIG. 1 is a plan view of a subcutaneous tunnelling device according to one embodiment of the present invention.
Figure 2:
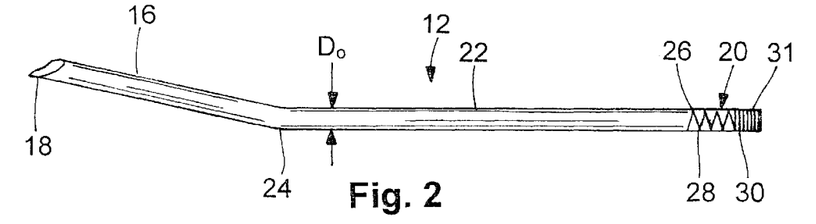
FIG. 2 is a plan view of the trocar of FIG. 1.
Figure 3:
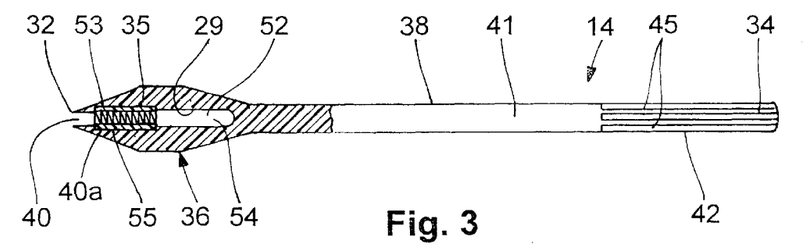
FIG. 3 is a partially broken away cross sectional view of the dilator of FIG. 1.

Referring now to the drawings in detail, there is shown in FIGS. 1–3 a preferred embodiment of a subcutaneous tunnelling device, generally referred to as 10, comprised of a trocar 12 and a dilator 14 removably attached to the trocar 12. Referring to FIGS. 1 and 2, the trocar 12 for forming a subcutaneous tunnel has a front end 16 having a point 18 configured for piercing skin and a rear end 20. As shown in FIG. 2, in the preferred embodiment, the trocar 12 is constructed from a solid rod 22 having a circular cross-section. A bend 24 is preferably disposed proximate the front end 16 of the trocar 12. However, it should be understood based on this disclosure that it is within the scope of the present invention to construct a hollow trocar 12 or a solid rod having other cross-sectional configurations, as long as the trocar 12 can function as described below.

Preferably, the trocar 12 includes a threaded peg 26 at the rear end 20 having a first thread 28 and a second thread 30. The first thread 28 is configured for engaging a threaded interior surface 29 of the dilator which defines a hole 52 as shown in FIG. 3. The second thread 30 is configured for engaging the interior surface of a catheter tube, as discussed below with respect to the method of the present invention.

Referring to FIGS. 1 and 3, the dilator 14 has a front end 32, a rear end 34, a preferably rigid dilating section 36 disposed between the front end 32 and the rear end 34. The dilator preferably also includes a rod section 38 extending rearwardly from the dilating section 36 as shown in FIG. 3. The front end 32 is configured for being removably attached to the rear end 20 of the trocar 12, as is described in detail below. Preferably, the dilating section 36 is disposed at the front end 32 of the dilator 14 such that the frontward edge 40 of the dilating section 36 is located at the front end 32 of the dilator 14. However, it should be understood based on this disclosure that the dilating section 36 may be disposed at various positions along the length of the dilator 14. For example, as shown in the alternative embodiment of FIG. 5, the frontward edge 40' of the dilating section 36' may be longitudinally spaced from the front end 32' of the dilator 14'. In such an embodiment, a front portion 39' of the rod section 38' extends outwardly from the frontward edge 40' of the dilating section 36'.

Referring to FIGS. 1 and 3, the dilator 14 has an exterior surface 41, at least a portion of which preferably includes an optional handle section 42 disposed on the rod section 38 near the rear end 34 of the dilator 14. Preferably, the handle section 42 of the dilator 14 includes a gripping surface such as the rib members 45 as shown in FIGS. 1 and 3. However, it would be understood, based on this disclosure, that other gripping surfaces could be used or that a gripping surface could be omitted within the scope of the invention. Examples of other gripping surfaces include a knurled rearward portion of the rod section 38 using conventional manufacturing techniques as shown in the alternative embodiment of FIG. 4. Further examples include a handle section 42 which has a portion of the rod section 38 having an outer diameter greater than the remainder of the rod section 38 (not shown), providing a separate handle member, such as a knob attached to the end 34 of the dilator (not shown) or by providing various other types of gripping surfaces.

Figure 4:
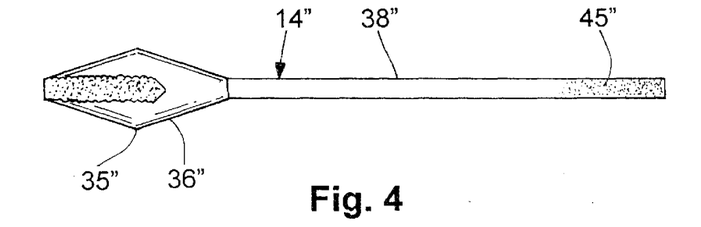
FIG. 4 is a plan view of an alternative embodiment of a dilator according to the present invention.
Figure 6:
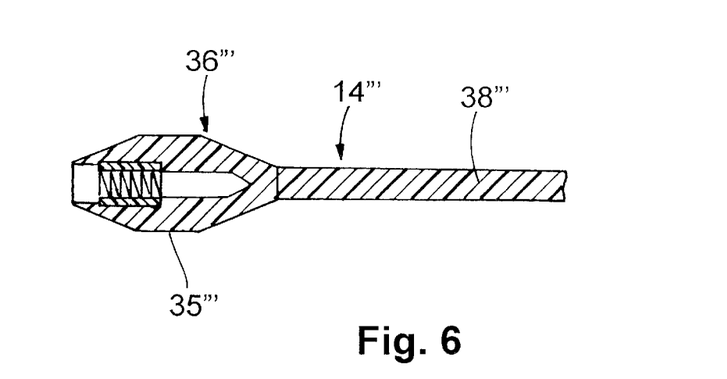
FIG. 6 is a partially broken cross-sectional view of an alternative embodiment of a dilator according to the present invention.
Figures 11, 12:
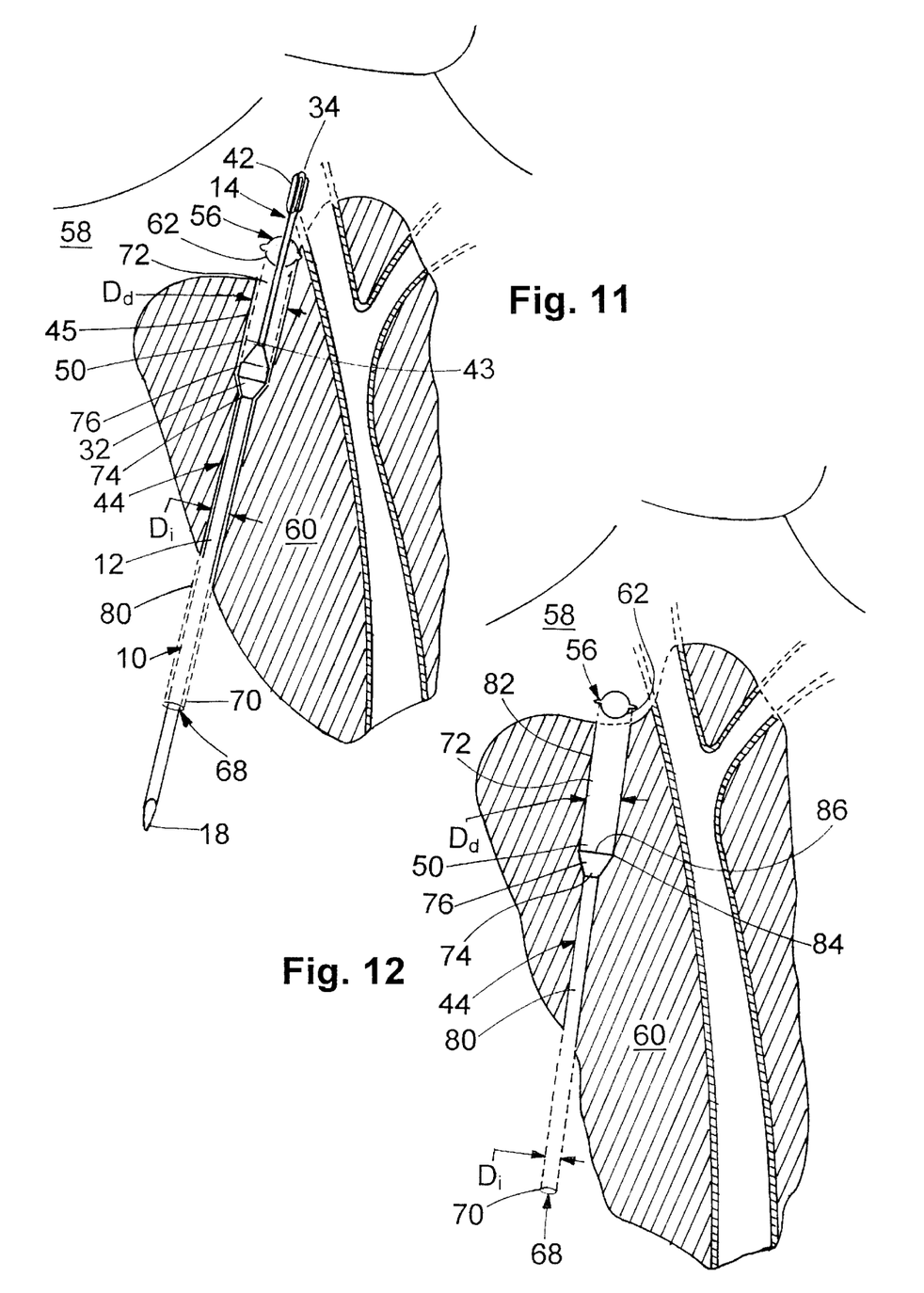
FIG. 11 is a partially broken-away view of the subcutaneous tunnelling device of FIG. 1 moving through the subcutaneous area and dilating a section of the tunnel.
FIG. 12 is a partially broken-away schematic view of a subcutaneous tunnel formed in accordance with the method of the present invention.

Referring to FIGS. 1 and 2, the dilating section 36 of the dilator 14 has a tapering outside diameter greater than the outside diameter $D_o$ of the trocar 12. Furthermore, the dilating section 36 has a maximum diameter $D_{max}$ sized for dilating an interior surface 43 of a subcutaneous tunnel 44 as shown in FIG. 11 and to enable seating of a stabilizing cuff 46 of a catheter 48 in a dilated tunnel section 50 of the tunnel 44, as is described in further detail below. In the preferred embodiment of the present invention, the dilating section 36 has a longitudinal cross-section which is generally octagonal as is best shown in FIGS. 1 and 3. Alternatively, as shown in FIG. 4, the dilating section 36" of dilator 14" may have a longitudinal cross-section generally shaped as a truncated diamond. A further alternative embodiment is shown in FIG. 6 and includes a dilator 14''' having a dilating section 36''' which has a longitudinal cross section generally shaped as a truncated ellipse. It should be understood that the cross-sectional configuration may be varied as long as the dilator 14 has a tapered outside diameter and can dilate a section of the subcutaneous tunnel as described below.

Preferably, the dilating section 36 has a transverse cross-section taken at any point along the longitudinal axis of the dilator which is generally circular, such that the maximum diameter $D_{max}$ discussed above is a true diameter. However, the present invention is intended to include a dilator 14 including a dilating section 36 having transverse cross-sections of any shape such as elliptical, figure-eight, rectangular and the like as long as the dilator 14 can function as described below. Therefore, the term "diameter" in this disclosure is herein defined as the maximum distance across a transverse cross-section. For example, a diameter of a dilating section 36 having quadrilateral-shaped or hexagonal-shaped transverse cross-sections would be the largest diagonal measurement across one of such cross-sections. Thus, the maximum diameter $D_{max}$, as discussed above, for a dilating section 36 having non-circular transverse cross-sections would be the maximum distance across the transverse crosssection having the greatest perimeter.

Referring to FIG. 3, the dilator 14 has an interior surface 29 which preferably defines an at least partially threaded hole 52 extending rearwardly from the front end 32 of the dilator 14. In the preferred embodiment, the trocar 12 includes a threaded peg 26 as shown in FIG. 2, and the threaded hole 52 of the dilator 14 is engageable with the threaded peg 26 of the trocar 12 to removably attach the dilator 14 to the trocar 12.

Preferably, the threaded hole 52 of the dilator 14 has a thread 53 configured to engage the first thread 28 of the threaded peg 26 of the trocar 12 and includes a clearance section 54 within which the rearward section 31 of the threaded peg 26, on which is disposed the second thread 30, is disposed when the dilator 14 is attached to the trocar 12. Other means for removably attaching the front end 32 of the dilator 14 to the rear end 20 of the trocar 12 may be used as alternatives to mating threads. For example, a quick-disconnect coupling between the trocar 12 and the dilator 14 or an extension connecting piece disposed between the trocar 12 and dilator 14. It should be understood, based on this disclosure, that any suitable method for attaching the front end 32 of the dilator 14 to the rear end 20 of the trocar 12 which does not interfere with tunnel formation may be used. The thread 53 within the hole 52 may be integrally formed within the dilating section 36 by injection molding or other molding process, or machined into the interior surface 29. Preferably, the thread 53 is included as an insert portion 55 set into the hole 52 and coupled to the interior surface 29 by adhesive, heat molding or any other method for attaching the two surfaces. Preferably, in such a case, the dilating portion 36 is formed with an indentation suitably sized to receive the insert portion 55 as shown in FIG. 3.

Figure 5:
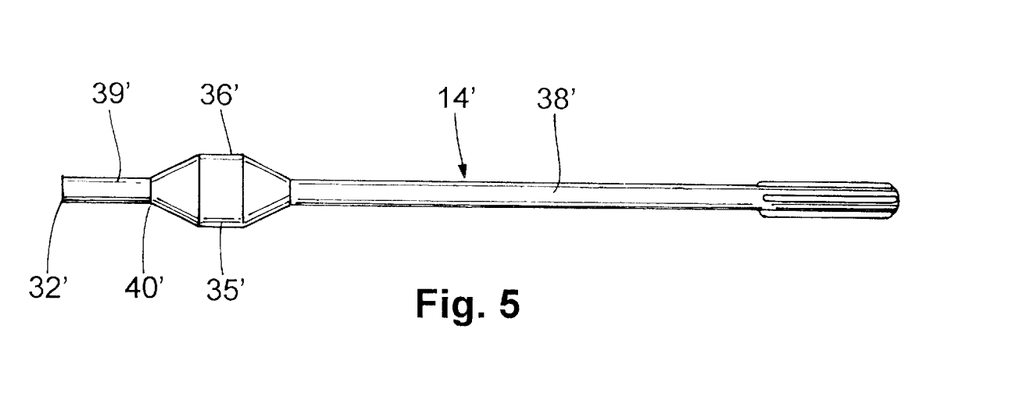
FIG. 5 is a plan view of a further alternative embodiment of a dilator according to the present invention.

In the preferred embodiment of the present invention, the trocar 12 is constructed of a rod of drawn steel, most preferably 303 stainless steel. The dilator 14 may be constructed from various materials, including metal, metal alloys and moldable polymeric and/or elastomeric material so long as the material has sufficient rigidity for dilating subcutaneous tissue. If formed of metal or metal alloy, the dilator 14 is preferably constructed of two pieces, a dilating section 36 of cast steel and a rod section 38 of drawn steel, both preferably 303 stainless steel, and joined together by braising. Most preferably, the dilator 14 is formed of a rigid plastic material, for example, a nylon, which is heat molded to the desired cross-sectional configuration. If an insert such as the insert portion 55 is used, it is preferably formed of 303 stainless steel or other suitable metal alloy and may be attached to the interior surface 29 of the dilating portion by any suitable method including adhesives and the like. It should be understood from this disclosure that it is within the scope of the present invention to construct the trocar 12 and the dilator 14 of other suitable materials which are sufficiently rigid to perform the function of the dilator 12 and which are capable of being sterilized, for example, other rigid plastic materials. Also, it is within the scope of the present invention, if metal or metal alloy is used, to construct the dilator 14 as a one-piece casting with the dilating section 36 being integral with the rod section 38 or to utilize other alternative means for joining the dilating section 36 to the rod section 38, such as mating threads, quick-connects and the like. Furthermore, it is within the scope of the present invention to construct a dilator 14 with a dilating section 36 that includes a center bore extending longitudinally therethrough and being located circumferentially around the outer wall of the rod section 38. This design is useful for the alternative design as shown in FIG. 5.

Figures 7, 8:
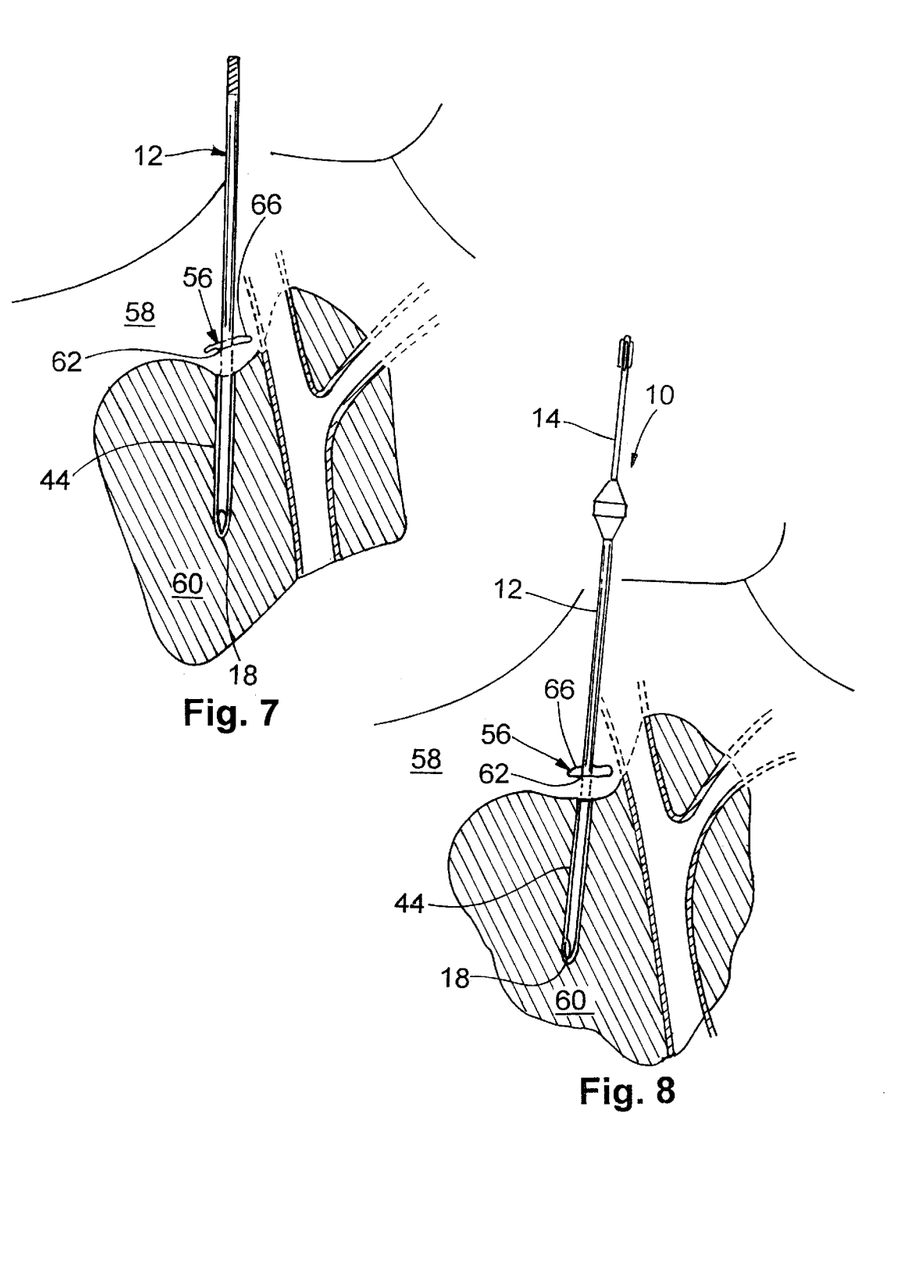
FIG. 7 is a partially broken-away diagrammatic view of the trocar of the device of FIG. 1 being inserted into the subcutaneous area according to the present invention.
FIG. 8 is a partially broken-away diagrammatic view of the subcutaneous tunnelling device of FIG. 1 being inserted into the subcutaneous area.
Figures 15, 16:
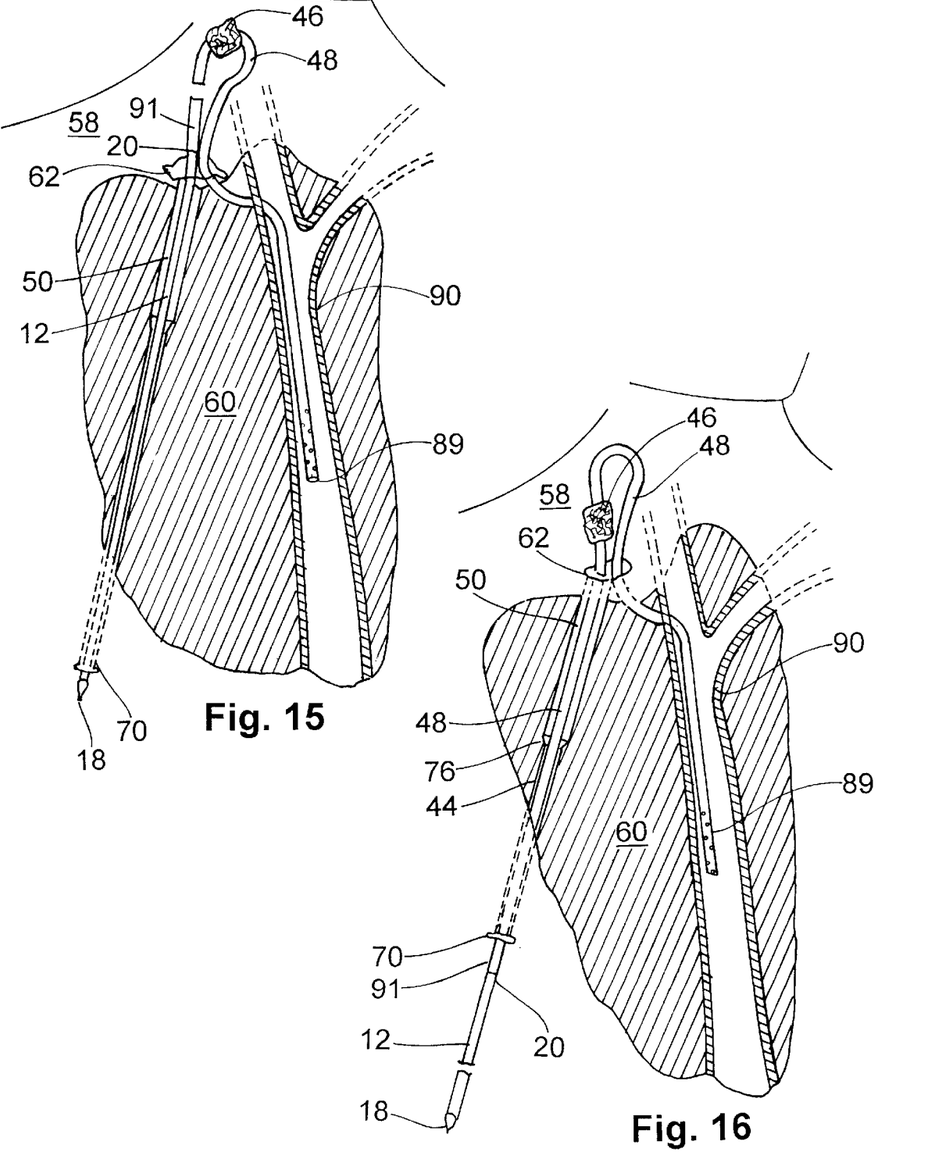
FIG. 15 is a partially broken-away view of a catheter having a distal end inserted in a vein and a proximal end attached to the trocar as shown in FIG. 14.
FIG. 16 is a partially broken-away diagrammatic view of a catheter being pulled through the tunnel.

Referring now to FIGS. 7–18, a preferred method of forming a subcutaneous tunnel 44 according to the present invention will now be described. The method will be described with reference to the subcutaneous tunnelling device 10 as described above, however, it should be understood that alternative devices as described or which are capable of performing the steps of the method may also be used. As shown in FIGS. 7 and 8, a trocar 12 is inserted through a first location 56 on a cutaneous surface 58 and moved through subcutaneous tissue 60 to partially form a subcutaneous tunnel 44 having a first end 62 near the first location 56. Preferably, in this method, the trocar 12 is not attached to the dilator 14 when the trocar is inserted through the cutaneous surface 58 and moved through the subcutaneous tissue 60 during this initial step. However, as shown in FIG. 8, in an alternative method, the trocar 12 may be inserted through the cutaneous surface 58 with the dilator 14 attached to the rear end 20 of the trocar 12 as the assembled tunnelling device 10. The first location 56 on the cutaneous surface 58 is preferably near the clavicle of the patient for one preferred use of the subcutaneous tunnel 44 in stabilizing a proximal portion of a catheter 48 in subcutaneous tissue while a distal portion of the catheter in located in the internal jugular vein 90 as shown in FIG. 15.

Preferably, an incision 66 is created at the first location 56 prior to inserting the trocar 12 through the cutaneous surface 58, such as by using a scalpel to cut through the cutaneous surface 58. However, it is within the scope of the present invention to directly pierce through the first location 56 on the cutaneous surface 58 with the point 18 of the trocar 12.

The incision 66 may also be used by the physician for aspirating the vessel in a manner known to those skilled in the art.

Figure 9:
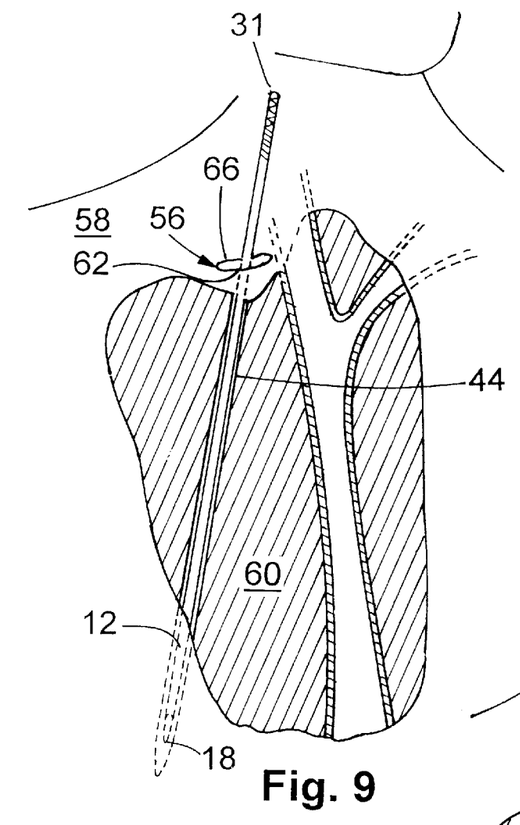
FIG. 9 is a partially broken-away view of a partially formed subcutaneous tunnel having a single cutaneous opening in accordance with one embodiment of the method of the present invention.
Figure 10:
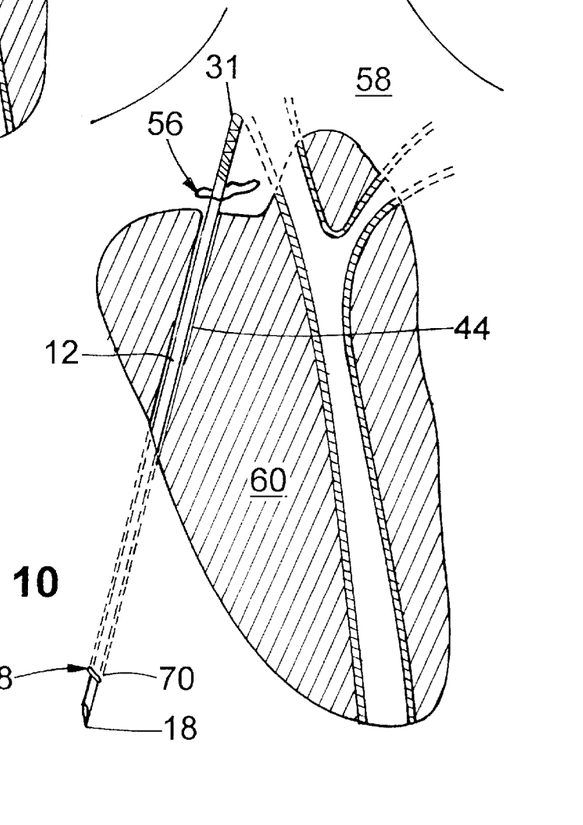
FIG. 10 is a partially broken-away view of an initially formed subcutaneous tunnel having two cutaneous openings in accordance with an alternative embodiment of the method of the present invention.

Furthermore, in one embodiment of the method, the movement of the trocar 12 through the subcutaneous tissue 60 is stopped within the subcutaneous tissue 60, preferably about ½" below the cutaneous surface 58 without again piercing through the cutaneous surface 58 at a different location. By not piercing the skin at this initial tunnelling step, bleeding during the tunnelling procedure may be minimized. At this point, the trocar 12 and tunnel appear as shown in FIG. 9, having a first, single cutaneous end 62, and the dilator 14 may be attached to the rear end of the trocar if it is not already attached as shown in FIG. 8. However, it is within the scope of the present invention to continue the movement of the trocar 12 until the trocar 12 pierces the cutaneous surface 60 at a second location 68, so that a second end 70 of the tunnel 44 is formed during the first step of the method. The dilator 14 is then attached to the end of the trocar when the trocar is positioned as shown in FIG. 10 wherein the tunnel has two cutaneous ends, the first end 62 and the second end 70.

As shown in FIG. 11, after at least partially forming the tunnel 44, the dilator 14 having a front end 32 attached to the trocar 12 is inserted as the device 10 into the tunnel 44, preferably through the first end 62. Although it is preferred to insert the dilator 14 into the first end 62 of the tunnel 44, it is within the scope of the present invention to insert the device 10 into the second end 70 of the tunnel 44 instead of the first end 62 for use with different catheter placement techniques.

In the preferred embodiment of the first method, the dilator 14 is attached to the trocar 12, as shown in FIG. 11, to form the subcutaneous tunnelling device 10, prior to inserting the dilator 14 into the first end 62 of the tunnel 44. The attachment of the dilator 14 to the trocar 12 is preferably accomplished by engaging the threaded hole 52 of the dilator 14 with the threaded peg 26 of the trocar 12, or other suitable connective means. The dilator is preferably attached when the second end 20 of the trocar 12 extends only slightly outside the first location 56 on the cutaneous surface 58.

Figure 13:
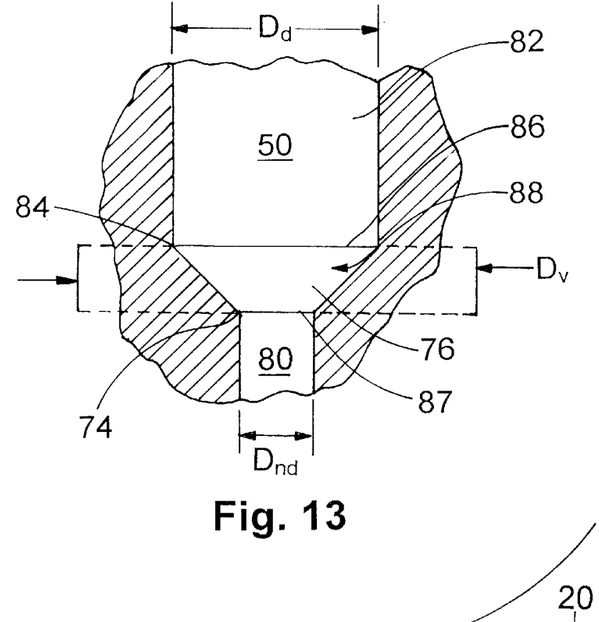
FIG. 13 is a greatly enlarged broken-away view of an end of a portion of the dilated section of the subcutaneous tunnel shown in FIG. 12.
Figure 14:
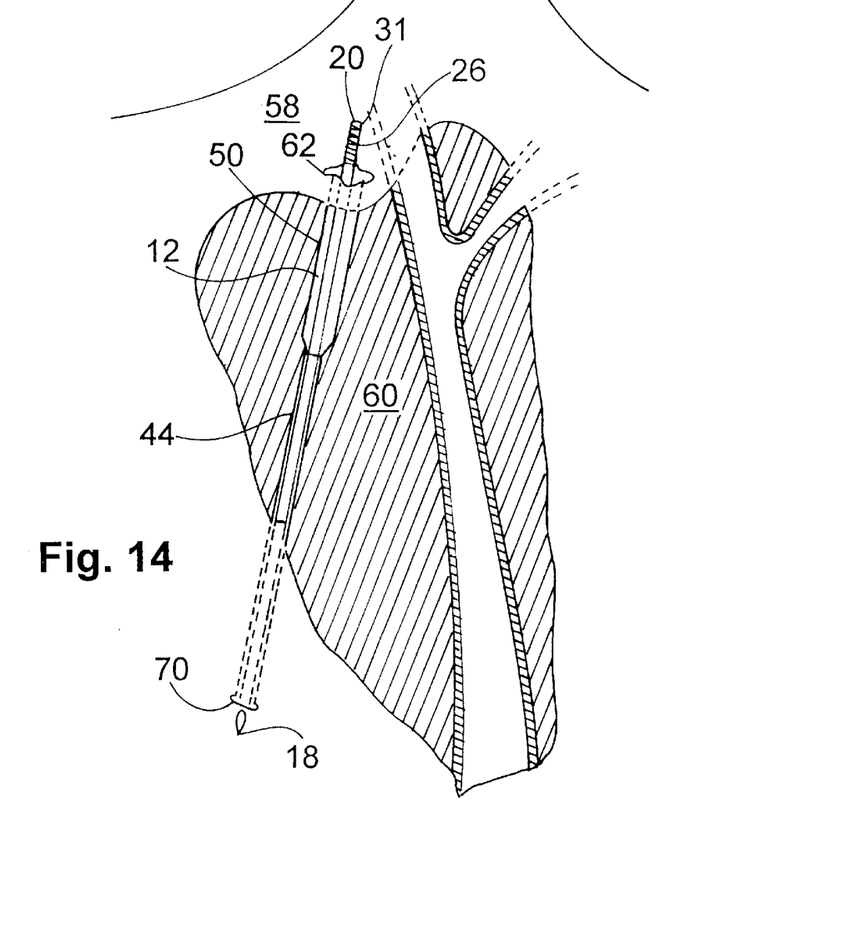
FIG. 14 is a partially broken-away view of the trocar of the subcutaneous tunnelling tool of FIG. 1 shown in FIG. 9 after the dilator has been detached with the end of the trocar extending out of the tunnel.

Once attached, as shown in FIG. 11, the dilator of the device 10 dilates a section 72 of the subcutaneous tunnel 44 by moving the dilator 14 partially through the tunnel 44 until the front end 32 of the dilator 14 reaches a predetermined first subcutaneous location 74 in the tunnel 44, thereby forming a dilated tunnel section 50 having a diameter $D_d$ approximately equal to the maximum diameter $D_{ma}x$ of the dilating section 36 and a subcutaneous end section 76 as best shown in FIG. 13. Dilation of the section 72 of the tunnel 44 to the increased diameter $D_d$ occurs due to the walls 45 of the subcutaneous tunnel 44 being pushed outwardly by the movement of the dilator 14 through the tunnel 44 initially formed by the trocar 12. The diameter expands from the diameter $D_i$ approximately equal to the outside diameter $D_o$ of the trocar 12 to the diameter $D_d$ as shown in FIG. 11. The trocar 12 is moved through the subcutaneous tunnel 44 prior to moving the dilator 12 through the tunnel 44.

In the preferred method, the point 18 of the trocar 12 will pierce through the second location 68 on the cutaneous surface 58 during dilation of the section 72 of the tunnel 44 to form the second end 70 of the tunnel 44 at the end of the non-dilated tunnel section 80. However, if the point 18 of the trocar 12 was already used to pierce through the second location 68 during the initial tunnelling step, the trocar 12 will simply slide through the already formed end 70 of the subcutaneous tunnel 44.

Preferably, for central venous catheterization procedures the subcutaneous location 74 is approximately 5 centimeters caudal to the first end 62 of the subcutaneous tunnel 44. However, it is within the scope of the present invention to move the front end 30 of the dilator 14 to any preferred subcutaneous location 74 in the tunnel 44 for various catheterization stabilizing procedures used when catheterizing various locations of the body such as other vessels, body cavities and the like. The present invention is intended to provide the person utilizing the subcutaneous tunnelling device 10 of the present invention with the ability to vary the location of the subcutaneous end 76 of the dilated tunnel section 50. This ability is limited by the length of the dilator 14, as the distance to which it is inserted into a tunnel 44 dictates the location of the subcutaneous end 76 of the dilated section 50 of the tunnel 44.

Finally, the dilator 14 is withdrawn from the dilated tunnel section 50 of the subcutaneous tunnel 44 through the first end 62 of the tunnel 44 preferably leaving the trocar partially extending out of tunnel. At this stage of the method of the present invention, a completed subcutaneous tunnel 44 including a dilated tunnel section 50 has been formed as shown in FIG. 12. FIG. 12 is intended only as a schematic drawing of the tunnel and it should be understood, based on this disclosure, that at this stage of the method, the trocar would still be within the tunnel 44. The physician can now detach the dilator and use the trocar for pulling the proximal portion of the catheter through the tunnel.

Referring to FIGS. 12 and 13, the subcutaneous tunnel 44 formed by the method of the present invention includes two sections, a dilated section 50 extending from the first end 62 to the subcutaneous location 74 and a non-dilated section 80 extending from the first subcutaneous location 74 to the second end 70. The non-dilated section 80 has a diameter $D_i$ approximately equal to the outside diameter $D_o$ of the trocar 12.

The dilated section 50 preferably includes two sections. First, a constant diameter section 82 extending from the first end 62 to the point of furthest travel 84 of the maximum diameter section 35 of the dilator 14, which forms the subcutaneous end 86 of the constant diameter section 82, and having a constant diameter $D_d$ approximately equal to the maximum diameter $D_{max}$ of the dilating section 36 of the dilator 14 as shown in FIG. 13. The dilated section 50 also includes a variable diameter section 88 extending from the subcutaneous end 86 of the constant diameter section 82 to the first subcutaneous location 74, which is the subcutaneous end 87 of the non-dilated section 80, with a variable diameter $D_v$ that approximately matches the profile of the frontward section 40a of the dilating section 36 of the dilator 14. Referring to FIG. 13, in the preferred configuration of the dilated tunnel section 50, which would be formed by utilizing a dilator 14 according to the present invention, the variable diameter section 88 is the subcutaneous end 76 of the dilated tunnel section 50.

The subcutaneous tunnel 44 created by the subcutaneous tunnelling device 10 and the method of the present invention has a variety of applications. Referring to FIGS. 14–17, a preferred use for a subcutaneous tunnel 44 formed by the tunnelling device 10 and the method of the present invention is for stabilizing a proximal end 91 of a catheter 48 after the distal end 89 has been positioned into a vein 90, another subcutaneous vessel, a body cavity or other area for removal or introduction of fluids. More specifically, the preferred use of the tunnel 44 for securing a catheter 48 is for a catheter 48 with a proximal end 91 having a stabilizing cuff 46, typically a fabric tissue ingrowth cuff, wrapped around its exterior. For such an application, the preferred method of the present invention further includes the following steps for inserting and stabilizing the catheter 48 within the subcutaneous tunnel 44.

Referring now to FIGS. 14–17, after forming the subcutaneous tunnel 44 including a dilated tunnel section 50, the dilator 14 is detached from the trocar 12. Preferably, the dilator 14 has been completely withdrawn as described above, with the trocar 12 of the tunnelling device 10 being situated within the tunnel 44 as shown in FIG. 15. The trocar 12 extends along the complete length of the tunnel 44. More specifically, the trocar 12 is situated within the tunnel 44 so that a portion of the front end 16 of the trocar 12 extends through the second end 70 of the tunnel 44 and a portion of the rear end 20 of the trocar 12 extends through the first end 62 of the tunnel 44, as shown in FIG. 15.

Next, a proximal end 91 of a catheter 48 having a stabilizing cuff 46 is attached to the rear end 20 of the trocar 12, as shown in FIG. 15. Preferably, this is accomplished by inserting the rearward end 31 of the threaded peg 26 of the trocar 12 into the luminal opening through the end 91 of the catheter 48 providing a friction fit between the interior surface of the catheter 48 and the second thread 30 of the threaded peg 26 of the trocar 12.

Next, as shown in FIG. 16, the trocar 12 is moved through the tunnel 44 to move the catheter 48 through the tunnel 44, so that the attached proximal end 91 of the catheter 48 moves from the first end 62 of the tunnel 44 to the second end 70 of the tunnel 44. Preferably, as described above, the trocar 12 is situated within the subcutaneous tunnel 44 so that the trocar 12 with the attached catheter 48 is pushed and then pulled through the tunnel 44. The trocar 12 and the attached catheter 48 are moved through the second end 70 of the tunnel 44 to exit the tunnel 44.

Figure 17:
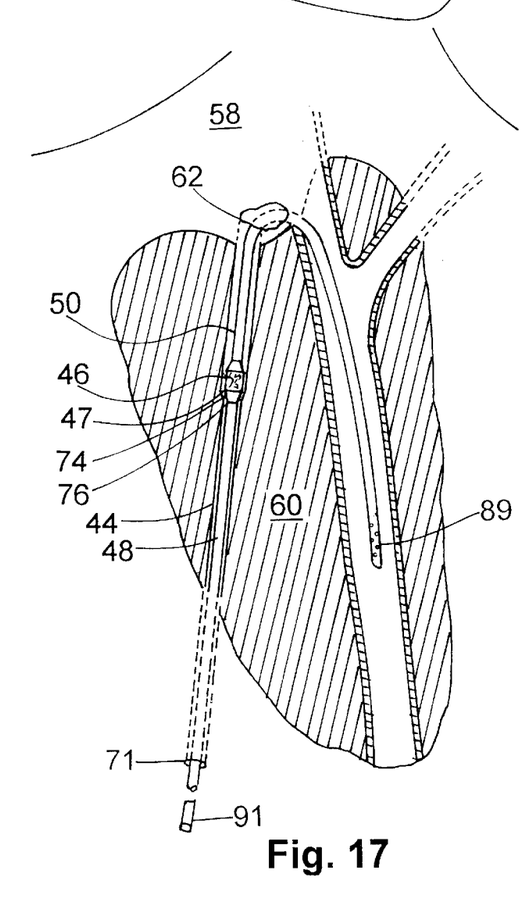
FIG. 17 is a partially broken-away diagrammatic view of a partially dilated subcutaneous tunnel with a catheter located in the tunnel with the securing cuff seated at the end of the dilated portion.
Figure 18:
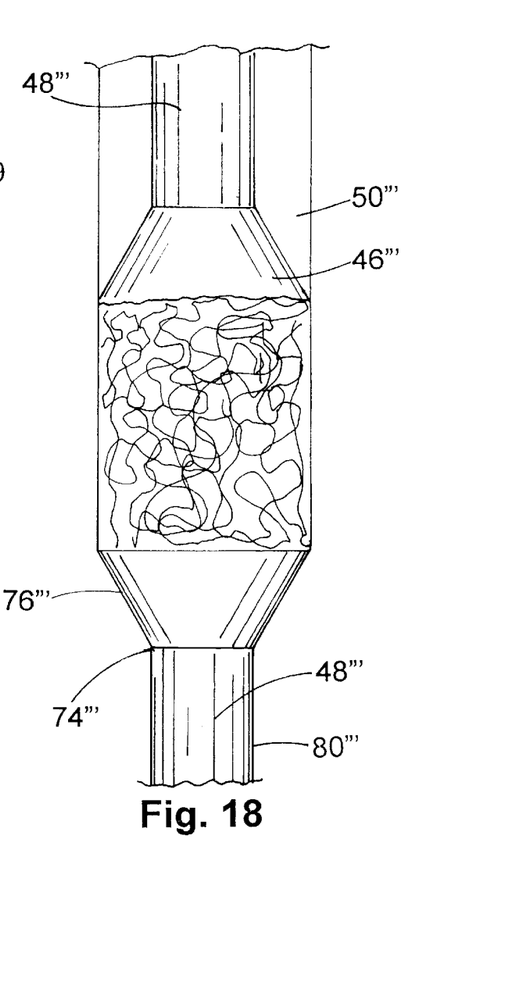
FIG. 18 is a greatly enlarged broken-away view of the end of the dilated section of the subcutaneous tunnel illustrating an alternative securing cuff seated in a variable diameter section of the subcutaneous end.

Finally, as shown in FIG. 17, the movement of the catheter 48 through the tunnel 44 is stopped when the stabilizing cuff 46 on the catheter 48 reaches the first subcutaneous location 74. Preferably, the front portion 47 of the stabilizing cuff 46 is seated within the variable diameter section 88 of the dilated tunnel section 50 as shown in FIG. 17. Seating the front portion 47 of a stabilizing cuff 46 in the variable diameter section 88 is especially preferred with an alternatively-shaped stabilizing cuff 46″″ which itself has a variable diameter portion, as shown in FIG. 18. The particular cuff shown in FIG. 18 is available from Medical Components, Inc. of Harleysville, Pa. and is the subject of co-pending U.S. patent application Ser. No. 08/611,927 incorporated herein by reference. In the embodiment shown in FIG. 18, the reference numbers correspond to similar reference numbers in other embodiments as shown in FIGS. 13–17 and as described herein, for example, catheter 48″″ corresponds to catheter 48, the difference in the embodiment of FIG. 18 being the type of cuff 46″″ as shown. However, it is within the scope of the present invention to seat the front portion 47 of any suitable stabilizing cuff 46 at the end 86 of the constant diameter section 82 of the dilated tunnel section 50 when the stabilizing cuff 46 has a diameter approximately equal to the diameter of the constant diameter section 82.

As the stabilizing cuff 46 abuts the end 76 of the dilated tunnel section 50, the cuff 46 is seated and there is a sudden tautness in the catheter 48. This alerts the surgeon or other medical personnel inserting the proximal end 91 of the catheter 48 in the tunnel that the cuff 46 is at the desired location and seated within the tunnel 44. A portion of the proximal end 91 of the catheter 48 extends outwardly from the second end 70 of the tunnel and may be secured externally on the cutaneous surface 58, such as, for example, by utilizing surgical tape. However, further securement is unnecessary.

The tunnelling methods of the present invention provide the dilated tunnel section 50 of the subcutaneous tunnel 44 which enables the catheter 48 to move without significant resistance from the subcutaneous tissue 60 through the subcutaneous tunnel 44 up to the subcutaneous end 76 of the dilated tunnel section 50. The diminished resistance to movement of the catheter 48 through the tunnel 44 due to the dilated tunnel section 50 provides advantages over prior art tunnelling procedures. The catheter 48 can be pulled through the tunnel 44 and easily located and seated in a predetermined position with minimal risk of snapping. Second, the surgeon or other medical personnel is alerted when the securing cuff 46 is successfully seated in the tunnel 44 by the tautness described.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A subcutaneous tunnelling device comprising:
   a trocar having a front end and a rear end, said front end having a point configured for piercing skin and said rear end configured for engaging the interior surface of a catheter tube for pulling a catheter tube through a subcutaneous tunnel; and
   a dilator having a front end, a rear end and a dilating section disposed between said front end and said rear end, said dilating section having a tapering outside diameter greater than an outside diameter of said trocar, said front end of said dilator being removably attached to said rear end of said trocar.

2. The tunnelling device according to claim 1, wherein said dilating section of said dilator has a maximum diameter sized for dilating an interior surface of a subcutaneous tunnel and for seating a catheter stabilizing cuff in a dilated subcutaneous tunnel.

3. The tunnelling device according to claim 1, wherein said dilating section has a generally octagonal longitudinal cross-section.

4. The tunnelling device according to claim 1, wherein said dilating section has a longitudinal cross-section generally shaped as a truncated ellipse.

5. The tunnelling device according to claim 1, wherein said dilating section is located at said front end of said dilator.

6. The tunnelling device according to claim 1, wherein said dilating section has a longitudinal cross-section generally shaped as a truncated diamond.

7. The tunnelling device according to claim 1, wherein said trocar has a threaded peg at said rear end and said dilator has an interior surface defining a hole at said front end, said interior surface comprising threads and said threads being engageable with said threaded peg to removably attach said dilator to said trocar.

8. The tunnelling device according to claim 7, wherein said peg of said trocar has a first thread and a second thread, said first thread being configured for engaging said threads of said dilator and said second thread being configured for engaging an interior surface of a catheter tube.

9. The tunnelling device according to claim 1, wherein said dilator has an exterior surface and at least a portion of said exterior surface of said dilator near said rear end of said dilator includes a gripping handle.

10. A dilator for dilating a section of a subcutaneous tunnel, said dilator comprised of:
   a front end configured for being removably attached to a trocar;
   a rear end; and
   a rigid dilating section disposed between said front end and said rear end, wherein said dilator is sufficiently rigid for dilating subcutaneous tissue.

11. The dilator according to claim 10, wherein said dilating section has a maximum diameter sized for dilating an interior surface of said subcutaneous tunnel and for seating a catheter stabilizing cuff in a dilated subcutaneous tunnel.

12. The dilator according to claim 10, wherein said dilating section has a generally octagonal longitudinal cross-section.

13. The dilator according to claim 10, wherein said dilating section has a longitudinal cross-section generally shaped as a truncated ellipse.

14. The dilator according to claim 10, wherein said dilating section has a longitudinal cross-section generally shaped as a truncated diamond.

15. The dilator according to claim 10, wherein said dilating section is located at said front end of said dilator.

16. A method of forming a subcutaneous tunnel, said method comprising the steps of:
   (a) inserting a trocar through a first location on a cutaneous surface and moving said trocar through subcutaneous tissue to form a subcutaneous tunnel having a first end near said first location;
   (b) attaching a dilator having a front end to said trocar;
   (c) dilating a section of said tunnel by moving said dilator partially through said tunnel until said front end of said dilator reaches a first subcutaneous location in said tunnel; and
   (d) withdrawing said dilator and said trocar at least partially from said dilated tunnel section of said subcutaneous tunnel through said first end of said tunnel.

17. The method according to claim 16, wherein step (a) further comprises stopping said movement of said trocar through said subcutaneous tissue within said subcutaneous tunnel without piercing through said cutaneous surface.

18. The method according to claim 16, wherein step (a) further comprises continuing said movement of said trocar until said trocar pierces said cutaneous surface at a second location.

19. The method according to claim 16, further comprising making an incision at said first location prior to inserting said trocar through said cutaneous surface.

20. The method according to claim 16, further comprising the steps of:
   (f) detaching said dilator from said trocar;
   (g) attaching a catheter having a stabilizing cuff to said trocar;
   (h) moving said trocar through said tunnel to move said catheter through said tunnel;
   (i) moving said trocar through a second end of said tunnel to exit said tunnel; and
   (1) stopping said movement of said catheter through said tunnel when said stabilizing cuff reaches said first subcutaneous location, thereby seating said cuff in said subcutaneous tunnel.

21. A method of forming a subcutaneous tunnel, said method comprising the steps of:
   (a) inserting a tunnelling device, including a trocar having a rear end and a dilator having a front end removably attached to said rear end of said trocar, through a first location on a cutaneous surface and moving said tunnelling device through subcutaneous tissue to form a subcutaneous tunnel having a first end near said first location;
   (b) dilating a section of said tunnel by moving said tunnelling device through said tunnel until said front end of said dilator reaches a first subcutaneous location in said tunnel; and
   (c) withdrawing said tunnelling device at least partially from said dilated tunnel through said first end of said tunnel.

22. The method according to claim 21, further comprising the steps of:
   (d) detaching said dilator from said trocar;
   (e) attaching a catheter having a stabilizing cuff to said trocar;
   (f) moving said trocar through said tunnel to move said catheter through said tunnel;
   (g) moving said trocar through a second end of said tunnel to exit said tunnel; and
   (h) stopping said movement of said catheter through said tunnel when said stabilizing cuff reaches said first subcutaneous location, thereby seating said cuff in said subcutaneous tunnel.

23. A device for forming a subcutaneous tunnel including a dilated tunnel section for securing a proximal end of a catheter when a distal end of the catheter is positioned in an area to be catheterized, said device comprising:
   a trocar for forming a subcutaneous tunnel, said trocar having a front end and a rear end, said front end having a point configured for piercing skin; and
   a dilator having a front end, a rear end and a dilating section disposed at said front end of said dilator, said dilating section having a tapering outside diameter including a maximum diameter sized for dilating an interior surface of a subcutaneous tunnel for seating a catheter stabilizing cuff in a dilated tunnel section and a generally octagonal longitudinal cross-section, said front end of said dilator being removably attached to said rear end of said trocar.

* * * * *